United States Patent [19]

Narutomi et al.

[11] Patent Number: 4,898,870
[45] Date of Patent: Feb. 6, 1990

[54] PYRROLOQUINOLINE QUINONE COMPOUNDS USEFUL AS AN ENZYME INHIBITOR

[75] Inventors: Yuji Narutomi, Kanagawa; Manabu Katsumata, Tokyo; Yasuko Osawa; Saburo Uchikuga, both of Kanagawa, all of Japan

[73] Assignee: Sogo Pharmaceutical Company Limited, Tokyo, Japan

[21] Appl. No.: 299,024

[22] Filed: Jan. 19, 1989

Related U.S. Application Data

[63] Continuation-in-part of Ser. No. 81,407, Jul. 31, 1987, abandoned.

[30] Foreign Application Priority Data

| Aug. 7, 1986 | [JP] | Japan | 61-184127 |
| Aug. 14, 1986 | [JP] | Japan | 61-189542 |
| Mar. 3, 1987 | [JP] | Japan | 62-046771 |
| Jul. 27, 1987 | [JP] | Japan | 62-185365 |

[51] Int. Cl.$^4$ .......................................... A61K 31/47
[52] U.S. Cl. ..................................... 514/292; 546/84
[58] Field of Search ........................... 546/84; 514/292

[56] References Cited

PUBLICATIONS

Duine et al., European Journal of Biochemistry, vol. 108, pp. 187–192, 1980.

Chem. Abstr., vol. 93, No. 7,. 93:64554m, p. 376, Aug. 18, 1980.

Dvornik, "Aldose Reductase Inhibition", Chapter 5, pp. 328–353, 1987.

*Primary Examiner*—Mary C. Lee
*Assistant Examiner*—Zinna Northington-Davis
*Attorney, Agent, or Firm*—Browdy and Neimark

[57] ABSTRACT

The present invention concerns an enzyme inhibitor containing the compound represented by the following formula (I) as an effective ingredient:

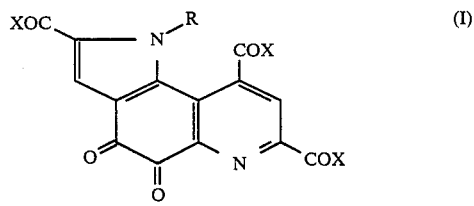

where R represents hydrogen or substituted or not substituted alkyl group, alkenyl group, aryl group or aralkyl group, X represents OR′ or NR″R‴, in which R′, R″ and R‴ represent respectively hydrogen or substituted or not substituted alkyl group, alkenyl group, aryl group or aralkyl group.

The enzyme inhibitor according to the present invention can effectively inhibit aldose reductase, glyoxalase I and reverse transcriptase.

1 Claim, No Drawings

PYRROLOQUINOLINE QUINONE COMPOUNDS USEFUL AS AN ENZYME INHIBITOR

This is a continuation-in-part of patent copending application Ser. No. 081,407, filed Jul. 31, 1987 now abandoned.

BACKGROUND OF THE INVENTION

1. Field of the Invention (Enzyme Inhibitor)

The present invention concerns an inhibitor containing pyrroloquinoline quinone and derivatives thereof as an effective ingredient against aldose reductase, glyoxalase I and reverse transcriptase.

The enzymes as the object of the enzyme inhibitor according to the present invention involve those enzymes selected from the group consisting of aldose reductase, glyoxalase I and reverse transcriptase.

(Aldose Reductase and Inhibitor Therefor)

Aldose reductase is an enzyme that generally acts at the first stage of a sorbitol pathway in which aldose, for example, glucose is converted into sorbitol under the presence of a coenzyme $NADPH_2$, further, formed into fructose under the action of sorbitol dehydrogenase and NAD, and then transferred into a glycolysis system. The pathway is represented by the following scheme.

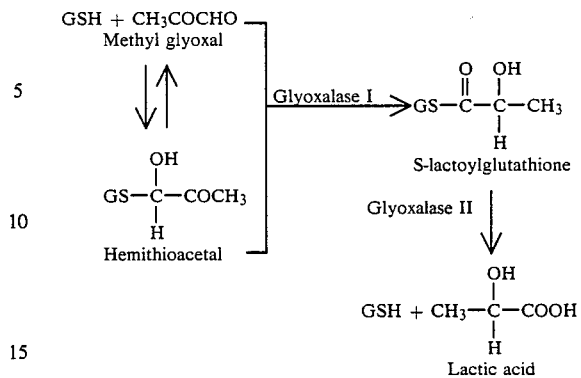

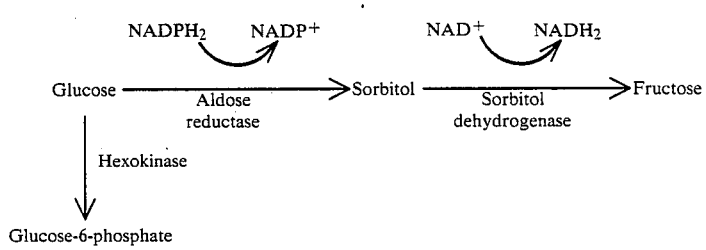

It has been known that although glucose is mainly put to a system in which it is converted by means of hexokinase to G-6-P and further decomposed into $CO_2$ to produce energy in the normal state, activities of hexokinase and sorbitol dehydrogenase are decreased, whereas the activity of aldose reductase is increased in the system of diabetes. Accordingly, glucose metabolism tends to proceed to the sorbitol pathway, by which sorbitol is accumulated within cells to induce diabetic complications such as diabetic cataract, diabetic ventinopathy, diabetic cornea, diabetic nephropathy and diabetic neuropathy. Accordingly, it is possible to prevent and cure diabetic complications by inhibiting the aldose reductase and various aldose reductase inhibitors have been studied and developed, but none of which has yet been put to practical use.

(Glyoxalase I and Inhibitor Therefor)

Generally, glyoxalase I is an enzyme contained in a glyoxalase system and contributes to the first step in a reaction of converting α-ketoaldehydes into α-hydroxy acids. It was discovered in 1913 that the glyoxalase system consists of two kinds of enzymes, that is, glyoxalase I and II and, a coenzyme glutathione (GSH). Glyoxalase I (lactoyl glutathionelyase, EC.4.4.1.5) converts hemithioacetal formed from GSH and methyl glyoxal into S-lactoylglutathione and this thioester is hydrolyzed into lactic acid and GSH under the effect of glyoxalase II (hydroxyacylglutathione hydrolase EC.3.1.2.6).

Methyl glyoxal is biologically synthesized in cells from dihydroxyacetone phosphate, glycerol and L-threonine. Methylglyoxal is a cytotoxin although it is formed in the cells. It has been known that methylglyoxal has a potent anti-cancer activity. However, its direct use as the anti-cancer agent has not been realized, because methyl glyoxal is rapidly converted by a glyoxalase system into an inactive S-lactoyl glutathione. It is said that the reaction is particularly remarkable in cancer cells. In view of the above, it has been attempted to accumulate methyl glyoxal by inhibiting glyoxalase I and, in the course of the study, the following two theories have become popular for the mechanism in which the glyoxalase I inhibitor exhibits an anti-cancer activity. One of them is that since glyoxalase I rapidly converts methyl glyoxal having cytotoxicity into lactic acid under the presence of GSH which is considered necessary for cell division, the glyoxalase I inhibitor causes accumulation of methyl glyoxal in cancer cells and, as a result, growth of cancer cells is hindered. The other theory is that since the growth of normal cells is delicately balanced between the growth suppressing effect (methyl glyoxal) and the growth promoting effect (glyoxalase I), the glyoxalase I inhibitor breaks the balance and, as a result, exhibits the anti-cancer activity.

Glyoxalase I inhibitors known so far include, for example, S-substituted GSH, ascorbic acid, lapachol and maltol. Although these inhibitors are effective in vitro, it has often been pointed out that they become invalid by decomposition and exhibit only weak activity of develope toxicity in vivo.

(Reverse Transcriptase and Inhibitor Therefor)

Genetic information is generally transcribed from DNA to RNA and translated into a protein. However, it has been disclosed by Temin that DNA is synthesized from RNA as a template and the genetic information is transcribed from RNA to DNA in RNA type tumour virus. The enzyme having such a type of activity is referred to as a reverse transcriptase.

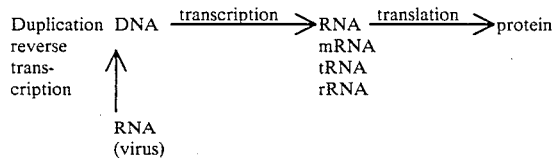

Presence of such enzymes have been found successively in various RNA type tumour virus recently and those virus having reverse transcriptase are referred to as retrovirus. Typical retrovirus include: Murine leukemia virus (MLV), Rous sarcoma virus (RSV), Avian myeloblastosis virus (AMV), Equine infectious anemia (EIA), Bovine leukemia virus (BLV), Pocine retrovirus, Manson-pfizer monkey virus (MPMV), Human T cell leukemia virus (HTLV), etc. and, particularly, HTLV-III has been noted as AIDS causing virus.

In the duplication of retrovirus, sub group of RNA virus is at first formed for the reverse transcription of genome RNA into DNA. Once the DNA has been formed, the genome of the virus is integrated into the cell genome of a host and utilizes the transcription/translation mechanism of host cell entirely for the purpose of duplication. Once integrated, the virus DNA can not substantially be distinguished from the host DNA by and the virus is stable against attack and can survive as it is as long as the life of the host cell is continued. Then, further new infection is caused. For the prevention and avoidance of new infection, it is necessary to inhibit the reverse transcriptase which plays a main role in the transmission of virus genetic information over a long period of a time, presumably, over the entire life of the host. Accordingly, the inhibitor should be so safe as allowable in view of its toxicity.

Although, tRNA (transfer-RNA) derivatives, Rifampicin derivatives, Carbopol 934, Pyran Copolymer, Phosphonoacetic acid, $\beta$-Lapachone, etc. are known as reverse transcriptase inhibitors at present, their in vivo toxicity has often been pointed out in view of their low specificity to the reverse transcriptase or their effectiveness only at a high concentration.

(Problems to be Solved by the Invention)

In view of the present situation as described above, the present inventors have made screening tests for various compounds. Since all of such enzymes are used for diseases requiring their administration for long period of time, it is required to develop those substances that can be administered for a long period of time and exhibit extremely low toxicity and we have a view that it is preferable to screen naturally occurring substances rather than artificially synthesized one. As a result, we have found that pyrroloquinoline quinone and derivatives thereof represented by the formula (I) are natural substances having potent inhibitory activity for aldose reductase, glyoxalase I and reverse transcriptase being safe as well and, as apparent from test examples described later, they have no problems at all in view of the toxicity, that is, they can be used as medical drugs as apparent from the acute toxicity test described later and, as a result of a further study, have accomplished the present invention:

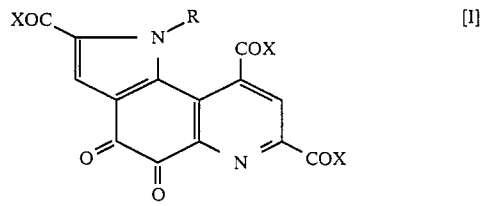

where R represents hydrogen or substituted or not substituted alkyl group, alkenyl group, aryl group or aralkyl group which may be substituted, X represents OR' or NR''R''', in which R', R'' and R''' represent hydrogen or substituted or not substituted alkyl group, alkenyl group, aryl group or aralkyl group.

Generally, pyrroloquinoline quinone (hereinafter referred to as PQQ) is a novel coenzyme different from conventional coenzyme NAD(P) or flavins for oxydation-reduction and it was initially found as a coenzyme for glucose dehydrogenase of Acinetobactor group. PQQ has a concern with the oxidizing reaction of alcohols, aldehydes, glucose and amines in an organism. Further, its growth promoting effect to a certain kind of micro-organisms, animal cells, plant cells has also been reported. Further, PQQ is also presented in the blood of mammal and, while its vitamin-like physiological activity is guessed, its biological roles has not yet been known at present. However, PQQ and its derivatives constitute the ingredients of an organism and considered to be a stable and non-toxic substance. This is apparent from the result of the acute toxicity test to mouse and rat described later.

TABLE 1

| Acute toxicity test of PQQ tri(dimethylamide) | | |
|---|---|---|
| | $LD_{50}$ (mg/kg) | |
| Kind of animal | oral | subcutaneous |
| Mouse | >5,000 | >1,500 |
| Rat | >5,000 | >1,500 |

The PQQ derivative represented by the formula (I) includes an oxidizing quinone and a reducing quinol. The quinone acts as an oxidizing agent and is reduced per se to a quinol. The quinol is again converted into the quinone if an adequate oxidizing agent is present. The quinone can easily form an adduct with alcohol, amine or other nucleophilic agent.

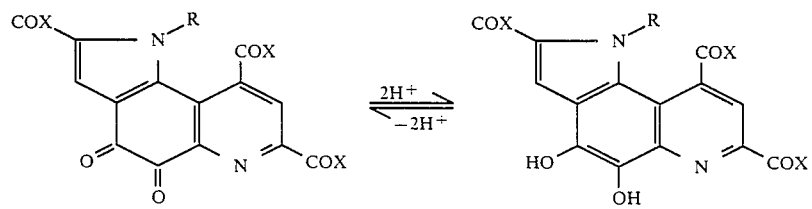

(formula I)

(where R and X have the same meanings as described above).

PQQ and its esters can be synthesized by the method of Corey, et al (E. J. Corey and Alfonso Tramontano, J. Am. Chem. Soc., 103, 5599–5600 (1981)). Triamide can be synthesized using PQQ intermediates. That is, as shown by the following reaction scheme, ester (1) as the intermediate product for the synthesis of PQQ is at first hydrolyzed to obtain a carboxylic acid (2). After converting the carboxylic acid (2) into acid chloride (3), it can be treated with dimethylamine to obtain an amide derivative (4). Finally, the amide derivative (4) is oxidized with ceric ammonium nitrate to produce PQQ tri(dimethylamide).

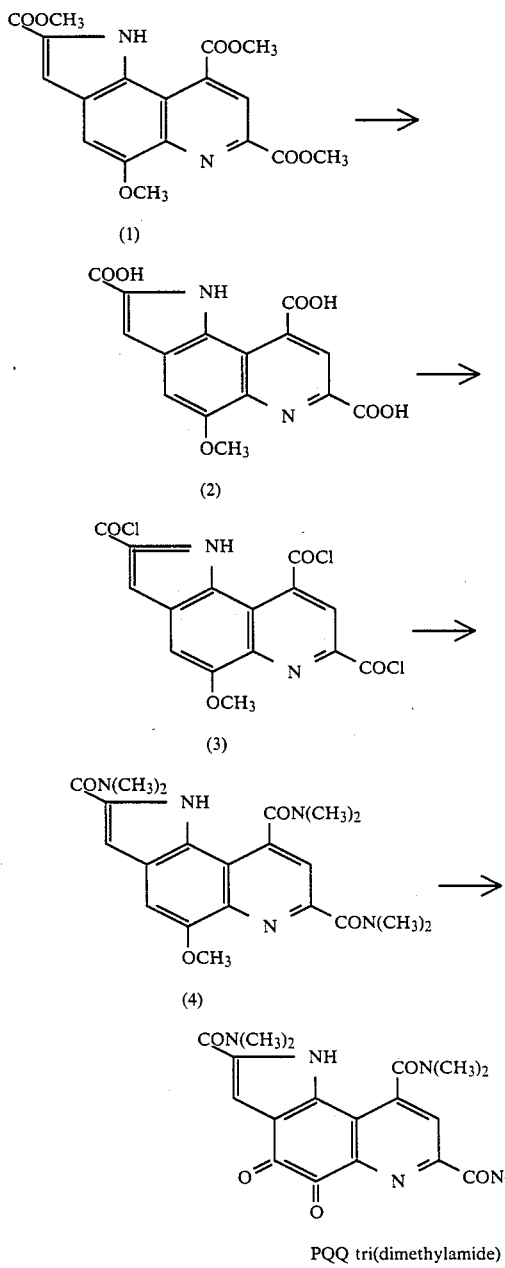

The enzyme inhibitor according to the present invention can be administered either orally or not orally. In the case of oral administration, they can be given in the form of soft or hard capsule, tablet, granule, fine granule and powder. Further, in the case of not-oral administration, they can be given as injection, solution, liquid and supossitory. In addition, slow releasing agent is also effective.

The dosage of the inhibitor according to the present invention is about from 0.1 to 300 mg/kg/day, preferably, from 0.2 to 200 mg/kg/day while different depending on the type, method of administration, symptom and age of patient, etc. It is preferably administered portionwise for 1 to 4 times and, preferably, 1 to 2 times per day.

For formulating the effective ingredient according to the present invention, surface active agent, shaping agent, lubricant, taste conditioner, odor conditioner, colorant, perfumes, preservation agent, suspending agent, wetting agent, film forming substance, coating aid and like other substance are appropriately used in accordance with ordinary manner. Further, it may be used optionally in combination with other inhibitors and medicines.

Test examples and examples will be described below for showing the inhibitory effect of the compound according to the present invention against aldose reductase, glyoxalase I and reverse transcriptase.

TEST EXAMPLE 1

Inhibitory Activity of PQQ Derivative for Rat Lens Aldose Reductase

A homogenate of rat lens was used and the activity of aldose reductase was measured by the method of Kinoshita, et. al. (Kinoshita J. H., et al, Metabolism, 28, 462–469, (1979)).

Specifically reaction was started by adding dl-glyceraldehyde as a substrate to a reaction solution containing rat lens homogenate, $Li_2SO_4$, $NADPH_2$ and inhibitor, and the enzyme activity was measured by the decrease of the optical absorption of $NADPH_2$ (optical density: OD) at 340 nm for 5 min. The solution with no addition of the substrate was used for the blank OD. The inhibiting ratio for the aldose reductase reaction by the inhibitor was determined by the following equation:

$$\text{Inhibiting ratio (\%)} = \left(1 - \frac{\text{Decrease in } OD \text{ in the presence of inhibitor} - \text{Decrease in } OD \text{ in the blank}}{\text{Decrease in } OD \text{ in the absence of inhibitor} - \text{Decrease in } OD \text{ in the blank}}\right) \times 100$$

The result is shown in Table 2.

TABLE 2

Inhibitory activity of PQQ derivatives for rat lens aldose reductase

| Inhibitor | $IC_{50}$ (M) |
|---|---|
| PQQ.2K | $2.0 \times 10^{-6}$ |
| PQQ.$H_2$ | $8.5 \times 10^{-6}$ |
| PQQ.3Me | $5.8 \times 10^{-6}$ |

PQQ.2K: PQQ dipotassium salt
PQQ.$H_2$ : PQQ reduced form
PQQ.3Me : PQQ trimethyl ester As apparent from the result it was found that PQQ derivatives have potent inhibitory activity against rat lens aldose reductase.

TEST EXAMPLE 2

Inhibitory Activity of PQQ Derivatives for Bovine Lens Aldose Reductase

The determination of enzyme activity was same as in Test Example 1 except enzyme source was bovine lens. The result is shown in Table 3.

TABLE 3

| Inhibitory activity of PQQ derivatives for bovine lens | |
|---|---|
| Inhibitor | $IC_{50}$ (M) |
| PQQ.2K | $3.0 \times 10^{-7}$ |
| PQQ.H$_2$ | $5.0 \times 10^{-6}$ |
| PQQ.3Me | $4.2 \times 10^{-6}$ |

As apparent from the result, it was found that PQQ derivatives have potent inhibitory activity against bovine lens aldose reductase.

TEST EXAMPLE 3

Inhibitory Activity of PQQ Derivatives for Human Placental Aldose Reductase

The determination of enzyme activity was same as in Test Example 1 except enzyme source was human placenta. The result is shown in Table 4.

TABLE 4

| Inhibitory activity of PQQ derivatives for human placental aldose reductase | |
|---|---|
| Inhibitor | $IC_{50}$ (M) |
| PQQ.2K | $1.9 \times 10^{-6}$ |
| PQQ.3Me | $3.9 \times 10^{-7}$ |
| PQQ.2Me.Et | $4.2 \times 10^{-7}$ |
| PQQ tri(dimethylamide) | $8.3 \times 10^{-7}$ |

PQQ.2Me.Et: PQQ dimethyl ethyl ester

As apparent from the result, it was found that PQQ derivatives has potent inhibitory activity against human placental aldose reductase.

TEST EXAMPLE 4

Inhibitory Action of PQQ Against Aldose Reductase

The activity of aldose reductase was measured according to the method of Kinoshita et al. [Metabolism, 28, 462-469 (1979)] using a homogenate of chick lens.

To a reaction solution containing the chick lens homogenate, $Li_2SO_4$, $NADPH_2$ and an inhibitor, was added dlglyceraldehyde as substrate to start the reaction, and the enzymatic activity was determined by measuring the decrease in optical density (OD) of $NADPH_2$ at 340 nm after five minutes. A solution with no substrate added was used for the blank test. The inhibition rate against the aldose reductase reaction was calculated from the following equation:

$$\text{Inhibition Rate (\%)} = \left(1 - \frac{\text{Decrease in } OD \text{ in the presence of inhibitor} - \text{Decrease in } OD \text{ in the blank}}{\text{Decrease in } OD \text{ in the absence of inhibitor} - \text{Decrease in } OD \text{ in the blank}}\right) \times 100$$

The result is shown in Table 5.

As can be seen from the table, PQQ inhibited the aldose reductase activity by 50% at a concentration of $5 \times 10^{-6}$M and by 100% at a concentration of $10^{-4}$M, indicating its powerful inhibitory action against aldose reductase.

TABLE 5

| Inhibitory action of PQQ against chick lens aldose reductase | |
|---|---|
| Inhibitor concentration (M/reaction soln.) | Inhibition Rate (%) |
| $10^{-8}$ | 0 |
| $10^{-7}$ | 0 |
| $10^{-6}$ | 13.9 |
| $10^{-5}$ | 82.1 |
| $10^{-4}$ | 100 |

TEST EXAMPLE 5

Inhibitory Action of PQQ Against Bovine Lens Aldose Reductase

A homogenate of bovine lens was centrifuged for ten minutes at 20,000 rpm under cooling, the supernatant was collected as an enzyme solution, and the inhibitory action of PQQ against aldose reductase was measured in the same way as in Test Example 4. The result is shown in Table 6.

TABLE 6

| Inhibitory action of PQQ against bovine lens aldose reductase | |
|---|---|
| Inhibitor concentration (M/reaction soln.) | Inhibition Rate (%) |
| $10^{-8}$ | 0 |
| $10^{-7}$ | 35.9 |
| $10^{-6}$ | 100 |
| $10^{-5}$ | 100 |

As can be seen from the table, PQQ acted more powerfully upon aldose reductase of bovine lens than upon that of check lens, inhibiting the reductase activity by 50% at a concentration as low as $3 \times 10^{-7}$M and by 100% at a concentration of $10^{-6}$M.

PQQ thus proved to have a powerful inhibitory action against aldose reductase.

TEST EXAMPLE 6

Effect of PQQ Upon Galactose-Induced Cataract

Male, Sprague-Dawley rats weighing 55 to 65 grams were used as test animals in this experiment. These were divided into three groups (normal group, 50%-galactose feed group, and drug-administered group). The normal group was given a commercial powdery feed (CE-2 of Clea Japan Inc.), and the other two groups were given the above normal feed further containing 50% galactose, with free access thereto in all cases.

To the drug-administered group, was further administered PQQ orally (30 mg/Kg) or intraperitonealy (20 mg/Kg) once a day throughout the course of test.

The lens was extracted from the test animals on the 7th and 10th days after the start of experiment, and cataract estimation was made according to the following standards:

| | |
|---|---|
| $A^-$ | No cloudiness; indistinguishable from the normal group |
| $A^0$ | Slight nebula in the cortex |
| $A^{00}$ | Medium degree of nebula in the cortex |
| $A^+$ | High degree of nebula in the cortex |
| $A^{++}$ | High degree of nebula in the cortex and slight cloudiness in the nucleus |

-continued

| | |
|---|---|
| A+++ | High degree of nebula in the nucleus |

The result is shown in Table 7.

TABLE 7

| Group | Day of Estimation | Grade | | | | | |
|---|---|---|---|---|---|---|---|
| | | A− | A⁰ | A⁰⁰ | A+ | A++ | A+++ |
| Normal group | 7th day | 2/2 | | | | | |
| 50%-Galactose feed group Drug-administered group | 7th day | | | 2/6 | 3/6 | 1/6 | |
| PQQ 30 mg/Kg p.o. | 7th day | 6/6 | | | | | |
| PQQ 20 mg/Kg i.p. | 7th day | 4/4 | | | | | |
| Normal group | 10th day | 4/4 | | | | | |
| 50%-Galactose feed group Drug-administered group | 10th day | | | | | 4/4 | |
| PQQ 30 mg/Kg p.o. | 10th day | | | | 4/4 | | |
| PQQ 20 mg/Kg i.p. | 10th day | | | 2/2 | | | | p.o.: oral administration, i.p.: intraperitoneal administration

As can be seen from the table, nebula (A⁰, A⁰⁰, A+) was formed in the eyes of rats kept on 50%-galactose feed for seven days, whereas no such nebula formation was observed at all in the drug-administered group (both p.o. and i.p.), indicating the effect of PQQ to retard nebula formation.

When keeping on 50%-galactose feed over a period of ten days, nebula of higher degree (grade A+) was formed in all the rats of this group, while improvement by two grades was observed with the drug-administered group.

The above result shows the effect of PQQ to retard the progress of cataract.

TEST EXAMPLE 7

Effect of PQQ Upon Egg Cataract Induced by Hydrocortisone

White-leghorn eggs were incubated in a hatcher held at a temperature of 37° C. and a relative humidity of about 70%.

To the control and drug-administered groups, was administered at the air space 0.2 ml each of a solution of 0.12 mg hydrocortisone succinate (HC) in pure water on the 15th day after the start of incubation.

To the drug-administered group, was further injected PQQ 2 hours, or 2 and 5 hours, after HC administration.

The lens was extracted from each egg 48 hours after HC administration, and cataract estimation was made by the method of Nishigohri et al. [INVESTIGATIVE OPHTHALMOLOGY & VISUAL SCIENCE, 25, 1051 (1984)] according to the following standards:

| | |
|---|---|
| I | No cloudiness in the lens; indistinguishable from the normal lens |
| II | Indistict opaque ring |
| III | Distinct turbid ring |
| IV | Clear areas of pinhole size left in turbid nucleus |
| V | Nucleus turbid over the whole area |

TABLE 8

| Group | Grade | | | | |
|---|---|---|---|---|---|
| | I | II | III | IV | V |
| Normal group | 2/2 | | | | |
| Control group HC 0.12 mg/egg | | | | | 4/4 |
| Drug-administered group | | | | | |
| PQQ 0.25 mg/egg × 1 | 2/8 | | | 4/8 | 2/8 |
| PQQ 0.5 mg/egg × 1 | 2/10 | | | 8/10 | |
| PQQ 0.5 mg/egg × 2 | | | 8/10 | 2/10 | |
| PQQ 1.0 mg/egg × 1 | 2/6 | 2/6 | 2/6 | | |

When 0.12 mg HC was administered on the 15th day from the start of incubation, cataract of grade V was observed on the 17th day, whereas PQQ evidently showed an effect of curing cataract.

TEST EXAMPLE 8

Inhibitory Action of PQQ·H₂ Against Chick Lens Aldose Reductase

An enzyme solution was prepared from chick lens in the same manner as in Test Example 4, and the inhibitory action of PQQ·H₂ against aldose reductase was measured in the same way as in Test Example 4. The result is shown in Table 9.

TABLE 9

| Inhibitory action of PQQ.H₂ against chick lens aldose reductase | |
|---|---|
| Inhibitor concentration (M/reaction soln.) | Inhibition Rate (%) |
| $10^{-7}$ | 0 |
| $10^{-6}$ | 31.8 |
| $10^{-5}$ | 62.1 |
| $2 \times 10^{-5}$ | 68.4 |
| $4 \times 10^{-5}$ | 92.8 |
| $6 \times 10^{-5}$ | 100 |
| $8 \times 10^{-5}$ | 100 |
| $10^{-4}$ | 100 |

As can be seen from the table, PQQ·H₂ inhibited the aldose reductase activity by 50% at a concentration of $6 \times 10^{-6}$M and by 100% at a concentration of $6 \times 10^{-5}$M, indicating that PQQ·H₂, which is a reduced form of PQQ, also has a powerful inhibitory action against chick lens aldose reductase.

TEST EXAMPLE 9

Inhibitory Action of PQQ·H₂ Against Bovine Lens Aldose Reductase

A homogenate of bovine lens was centrifuged for ten minutes at 20,000 rpm under cooling, the supernatant was collected as an enzyme solution, and the inhibitory action of PQQ·H₂ against bovine lens aldose reductase was measured in the same way as in Test Example 4. The result is shown in Table 10.

TABLE 10

| Inhibitory action of PQQ.H₂ against bovine lens aldose reductase | |
|---|---|
| Inhibitor concentration (M/reaction soln.) | Inhibition Rate (%) |
| $10^{-7}$ | 0 |
| $10^{-6}$ | 0 |
| $4 \times 10^{-6}$ | 27.8 |
| $6 \times 10^{-6}$ | 89.9 |
| $8 \times 10^{-6}$ | 100 |
| $10^{-5}$ | 100 |
| $10^{-4}$ | 100 |

As can be seen from the table, PQQ·H$_2$ inhibited the activity of bovine lens aldose reductase by 50% at a concentration of $5\times10^{-6}$M and by 100% at a concentration of $8\times10^{-6}$M, indicating that PQQ·H$_2$ also has a powerful inhibitory action against bovine lens aldose reductase.

TEST EXAMPLE 10

Inhibitory Action of PQQ·H$_2$ Against Rat Lens Aldose Reductase

A homogenate of rat lens was centrifuged for four minutes at 3,000 rpm under cooling, the supernatant was collected as an enzyme solution, and the inhibitory action of PQQ·H$_2$ against aldose reductase was measured in the same way as in Test Example 4. The result is shown in Table 11.

TABLE 11

Inhibitory action of PQQ.H$_2$ against rat lens aldose reductase

| Inhibitor concentration (M/reaction soln.) | Inhibition Rate (%) |
|---|---|
| | 0 |
| $10^{-6}$ | 15.1 |
| $10^{-5}$ | 59.5 |
| $2\times10^{-5}$ | 100 |

As can be seen from the table, PQQ·H$_2$ inhibited the activity of rat lens aldose reductase by 50% at a concentration of $8.5\times10^{-6}$M and by 100% at a concentration of $2\times10^{-5}$M, indicating that PQQ·H$_2$ also has a powerful inhibitory action against rat lens aldose reductase.

TEST EXAMPLE 11

Inhibitory Action of PQQ·3Me Against Chick Lens Aldose Reductase

An enzyme solution was prepared from chick lens in the same manner as in Test Example 4, and the inhibitory action of PQQ·3Me against aldose reductase was measured in the same way as in Test Example 4. The result is shown in Table 12.

TABLE 12

Inhibitory action of PQQ.3Me against chick lens aldose reductase

| Inhibitor concentration (M/reaction soln.) | Inhibition Rate (%) |
|---|---|
| $10^{-6}$ | 0 |
| $2\times10^{-6}$ | 30.0 |
| $4\times10^{-6}$ | 77.1 |
| $6\times10^{-6}$ | 87.1 |
| $8\times10^{-6}$ | 100 |
| $10^{-5}$ | 100 |

As can be seen from the table, PQQ·3Me inhibited the activity of chick lens aldose reductase by 50% at a concentration of $3\times10^{-6}$M and by 100% at a concentration of $8\times10^{-6}$M, indicating that PQQ·3Me has an inhibitory action against chick lens aldose reductase.

TEST EXAMPLE 12

Inhibitory Action of PQQ·3Me Against Bovine Lens Aldose Reductase

An enzyme solution was prepared from chick lens in the same manner as in Test Example 9, and the inhibitory action of PQQ·3Me against bovine lens aldose reductase was measured in the same way as in Test Example 4. The result is shown in Table 13.

TABLE 13

Inhibitory action of PQQ.3Me against bovine lens aldose reductase

| Inhibitor concentration (M/reaction soln.) | Inhibition Rate (%) |
|---|---|
| $10^{-7}$ | 0 |
| $10^{-6}$ | 10.0 |
| $2\times10^{-6}$ | 22.6 |
| $4\times10^{-6}$ | 45.8 |
| $6\times10^{-6}$ | 100 |
| $8\times10^{-6}$ | 100 |
| $10^{-5}$ | 100 |

As can be seen from the table, PQQ·3Me was effective at concentrations of $10^{-6}$M and higher, inhibiting the activity of chick lens aldose reductase by 50% at a concentration of $4.2\times10^{-6}$M and by 100% at a concentration of $6\times10^{-6}$M. PQQ·3Me thus proved to have an inhibitory action also against bovine lens aldose reductase.

TEST EXAMPLE 13

Inhibitory Action of PQQ·3Me Against Rat Lens Aldose Reductase

An enzyme solution was prepared from rat lens in the same manner as in Test Example 10, and the inhibitory action of PQQ·3Me against rat lens aldose reductase was measured in the same way as in Test Example 4. The result is shown in Table 14.

TABLE 14

Inhibitory action of PQQ.3Me against rat lens aldose reductase

| Inhibitor concentration (M/reaction soln.) | Inhibition Rate (%) |
|---|---|
| $10^{-6}$ | 0 |
| $2\times10^{-6}$ | 3.3 |
| $4\times10^{-6}$ | 23.5 |
| $6\times10^{-6}$ | 54.4 |
| $8\times10^{-6}$ | 98.9 |
| $10^{-5}$ | 100 |
| $10^{-4}$ | 100 |

As can be seen from the table, PQQ·3Me inhibited the activity of rat lens aldose reductase by 50% at a concentration of $5.8\times10^{-6}$M and by 100% at a concentration of $10^{-5}$M, indicating that it also has an inhibitory action against rat lens aldose reductase.

TEST EXAMPLE 14

Inhibitory Action of PQQ·2K Against Human Placental Aldose Reductase

An enzyme solution was prepared from human placenta, and the inhibitory action of PQQ·2K against human placental aldose reductase was measured in the same way as in Test Example 4. The result is shown in Table 15.

TABLE 15

Inhibitory action of PQQ.2k against human placental aldose reductase

| Inhibitor concentration (M/reaction soln.) | Inhibition Rate (%) |
|---|---|
| $9\times10^{-7}$ | 8.3 |
| $10^{-6}$ | 26.9 |
| $2\times10^{-6}$ | 51.4 |
| $3\times10^{-6}$ | 83.3 |
| $4\times10^{-6}$ | 100 |

As can be seen from the table, PQQ·2K inhibited the activity of human placental aldose reductase by 50% at a concentration of $1.92 \times 10^{-6}$M and by 100% at a concentration of $4 \times 10^{-6}$M, indicating that it has an inhibitory action against not only lens aldose reductase of various animals but also human placental aldose reductase.

TEST EXAMPLE 15

Inhibitory Action of PQQ·3Me Against Human Placental Aldose Reductase

An enzyme solution was prepared from human placenta, and the inhibitory action of PQQ·3Me against human placental aldose reductase was measured in the same way as in Test Example 4. The result is shown in Table 16.

TABLE 16

Inhibitory action of PQQ.3Me against human placental aldose reductase

| Inhibitor concentration (M/reaction soln.) | Inhibition Rate (%) |
|---|---|
| $8 \times 10^{-8}$ | 1.7 |
| $10^{-7}$ | 10.0 |
| $2 \times 10^{-7}$ | 15.0 |
| $3 \times 10^{-7}$ | 34.4 |
| $4 \times 10^{-7}$ | 50.6 |
| $5 \times 10^{-7}$ | 63.9 |
| $2.5 \times 10^{-6}$ | 100 |
| $5 \times 10^{-6}$ | 100 |

As can be seen from the table, PQQ·3Me showed a more powerful inhibitory action against human placental aldose reductase than PQQ·2K, inhibiting its activity by 50% at a concentration of $3.9 \times 10^{-7}$M and by 100% at a concentration of $2.5 \times 10^{-6}$M. PQQ·3Me thus proved to have a powerful inhibitory action against human placental aldose reductase.

TEST EXAMPLE 16

Inhibitory Action of PQQ·2Me.Et Against Human Placental Aldose Reductase

An enzyme solution was prepared from human placenta, and the inhibitory action of PQQ·2Me.Et against human placental aldose reductase was measured in the same way as in Test Example 4. The result is shown in Table 17.

TABLE 17

Inhibitory action of PQQ.2Me.Et against human placental aldose reductase

| Inhibitor concentration (M/reaction soln.) | Inhibition Rate (%) |
|---|---|
| $10^{-7}$ | 0 |
| $2 \times 10^{-7}$ | 17.6 |
| $3 \times 10^{-7}$ | 29.3 |
| $4 \times 10^{-7}$ | — |
| $5 \times 10^{-7}$ | 59.0 |
| $10^{-6}$ | 91.2 |
| $1.25 \times 10^{-6}$ | 97.1 |
| $2.5 \times 10^{-6}$ | 100 |

As can be seen from the table, PQQ·2Me.Et inhibited the activity of human placental aldose reductase by 50% at a concentration of $4.2 \times 10^{-7}$M and by 100% at a concentration of $2.5 \times 10^{-6}$M, indicating that it has a powerful inhibitory action against human placental aldose reductase nearly equal to that of PQQ·3Me.

As is apparent from the foregoing, PQQ derivatives show inhibitory action against not only lens aldose reductase of various animals but also human placental aldose reductase, and their action is most powerful against human placental aldose reductase.

EXAMPLE 1

Tablet

| 1 | PQQ tri(dimethylamide) | 50 g |
|---|---|---|
| 2 | Lactose | 90 g |
| 3 | Corn starch | 29 g |
| 4 | Magnesium stearate | 1 g |

The ingredients (1), (2) and 17 g of corn starch were mixed and granulated together with a paste prepared from 7 g of corn starch. 5 g of the corn starch and the ingredient (4) were added to the granules and compressed in a compression tabletor to prepare 1000 pieces of tablets each containing 50 mg of the ingredient (1).

EXAMPLE 2

Capsules

| 1 | PQQ.3Me | 200 g |
|---|---|---|
| 2 | Lactose | 150 g |
| 3 | Corn starch | 100 g |
| 4 | Crystalline cellulose | 40 g |
| 5 | Light anhydrous silisic acid | 5 g |
| 6 | Magnesium stearate | 5 g |

The above-mentioned ingredients were mixed with each other and granulated in a conventional manner and filled into 1000 pieces a capsules to prepare 1000 capsules each containing 200 mg of the ingredient (1).

EXAMPLE 3

Tablet

| 1 | PQQ tri(dimethylamide) | 200 g |
|---|---|---|
| 2 | Lactose | 100 g |
| 3 | Corn starch | 80 g |
| 4 | Crystalline cellulose | 100 g |
| 5 | Polyvinylpyrrolidone | 15 g |
| 6 | Magnesium stearate | 5 g |

The above-mentioned ingredients were mixed with each other and granulated in a conventional manner, which was compression molded to prepare 1000 tablets each containing 200 mg of the ingredient (1).

EXAMPLE 4

Injection Solution

| 1 | PQQ.2K | 5 g |
|---|---|---|
| 2 | Sodium chloride | 9 g |
| 3 | Chloro butanol | 5 g |
| 4 | Sodium hydrogen carbonate | 1 g |

All of the ingredients were dissolved in 1000 ml of distilled water and divisionally injected into ampours each by 1 ml to prepare 1000 units of injection solution.

What is claimed is:

1. A method for the therapy of preventing and treating diabetic complications by inhibiting aldose reductase, comprising administering to a patient in need of said therapy an amount sufficient for preventing or treating diabetic complications of a compound of the formula (I):

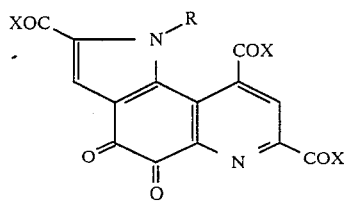
(I)
wherein R is hydrogen, X is OR' or NR''R''', and R', R'' and R'''' are each selected from the group consisting of hydrogen and lower alkyl.
* * * * *
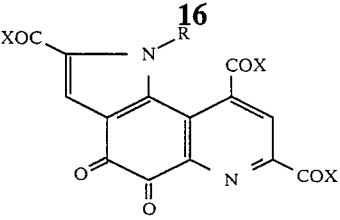
(I)
wherein R is hydrogen, X is OR' or NR''R''', and R', R'' and R'''' are each selected from the group consisting of hydrogen and lower alkyl.
* * * * *